US012709741B2

(12) United States Patent
Hennes

(10) Patent No.: US 12,709,741 B2
(45) Date of Patent: Aug. 18, 2026

(54) PHAGE CULTURING DEVICE, METHOD FOR PREPARING PHAGES, AND FILTRATION DEVICE FOR SAME

(71) Applicant: Kilian Hennes, Iserlohn (DE)

(72) Inventor: Kilian Hennes, Iserlohn (DE)

( * ) Notice: Subject to any disclaimer, the term of this patent is extended or adjusted under 35 U.S.C. 154(b) by 1099 days.

(21) Appl. No.: 17/785,958

(22) PCT Filed: Dec. 16, 2020

(86) PCT No.: PCT/EP2020/086464
§ 371 (c)(1),
(2) Date: Aug. 17, 2022

(87) PCT Pub. No.: WO2021/122776
PCT Pub. Date: Jun. 24, 2021

(65) Prior Publication Data
US 2023/0020806 A1 Jan. 19, 2023

(30) Foreign Application Priority Data
Dec. 16, 2019 (DE) ..................... 10 2019 134 489.1

(51) Int. Cl.
*C12N 7/00* (2006.01)
*C12M 1/00* (2006.01)
*C12M 1/26* (2006.01)

(52) U.S. Cl.
CPC ............... *C12N 7/00* (2013.01); *C12M 21/00* (2013.01); *C12M 23/26* (2013.01); *C12M 23/40* (2013.01);
(Continued)

(58) Field of Classification Search
None
See application file for complete search history.

(56) References Cited

U.S. PATENT DOCUMENTS 8,003,323 B2 8/2011 Morris et al.
8,685,695 B2 4/2014 Mueller
(Continued)

FOREIGN PATENT DOCUMENTS

DE 69530795 T2 3/2004
DE 60106727 T2 12/2005
(Continued)

OTHER PUBLICATIONS

Rodrigo Garcia et al., "Bacteriophage Production Models: An Overview", Frontiers in Mocrobiology, vol. 10, Jun. 4, 2019, XP055684147.
(Continued)

*Primary Examiner* — Henry H Nguyen
(74) *Attorney, Agent, or Firm* — Norris McLaughlin, P.A.

(57) ABSTRACT

A device and a method for clinically providing a preparation of autologous phages, namely, those that can verifiably be traced back to originating from a very specific person and preferably are also only intended for use in this one specific person includes a phage culturing device which is a fluid line system that is sealed off with respect to the outside environment The phages in the fluid line system obtained after at least one-time culturing are separated from bacteria by way of filtration, and preferably by way of tangential flow filtration. The phages separated by way of filtration are transferred into a collection vessel that is connected to the fluid line system and are preferably removed from the fluid line system, using the collection vessel, as a usable, preferably autologous preparation.

3 Claims, 1 Drawing Sheet

(52) U.S. Cl.
CPC ............ *C12M 29/04* (2013.01); *C12M 33/04* (2013.01); *C12N 2502/70* (2013.01)

(56) References Cited

U.S. PATENT DOCUMENTS

| | | | | |
|---|---|---|---|---|
| 10,031,080 | B2 | 7/2018 | Schmidt et al. | |
| 2004/0191892 | A1* | 9/2004 | Wicks | C12M 41/36 435/5 |
| 2012/0040329 | A1* | 2/2012 | Baldwin | C12N 7/00 435/235.1 |
| 2013/0059371 | A1* | 3/2013 | Shevitz | C12M 29/04 210/257.2 |
| 2013/0149759 | A1* | 6/2013 | Summer | C10L 1/026 435/235.1 |
| 2015/0158907 | A1* | 6/2015 | Zhou | C12M 41/00 530/399 |
| 2017/0298456 | A1* | 10/2017 | Holder | C12Y 301/00 |
| 2018/0230508 | A1 | 8/2018 | Idelevich et al. | |
| 2019/0241856 | A1* | 8/2019 | Wales | C12M 41/40 |
| 2021/0261900 | A1* | 8/2021 | Bhargav | B01D 65/02 |

FOREIGN PATENT DOCUMENTS

| | | | |
|---|---|---|---|
| DE | 102013225037 | A1 | 6/2015 |
| DE | 102015112343 | A1 | 2/2017 |
| EP | 2103308 | A1 | 9/2009 |
| WO | 96/01045 | A1 | 1/1996 |
| WO | 2014/048407 | A2 | 4/2014 |

OTHER PUBLICATIONS

Francesco Mancuso et al., "High Throughput Manufacturing of Bacteriophages Using Continuous Stirred Tank Bioreactors Connected in Series to Ensure Optimum Host Bacteria Physiology for Phage Production", Viruses, vol. 10, No. 10, Oct. 1, 2018, p. 537, XP055772356.

* cited by examiner

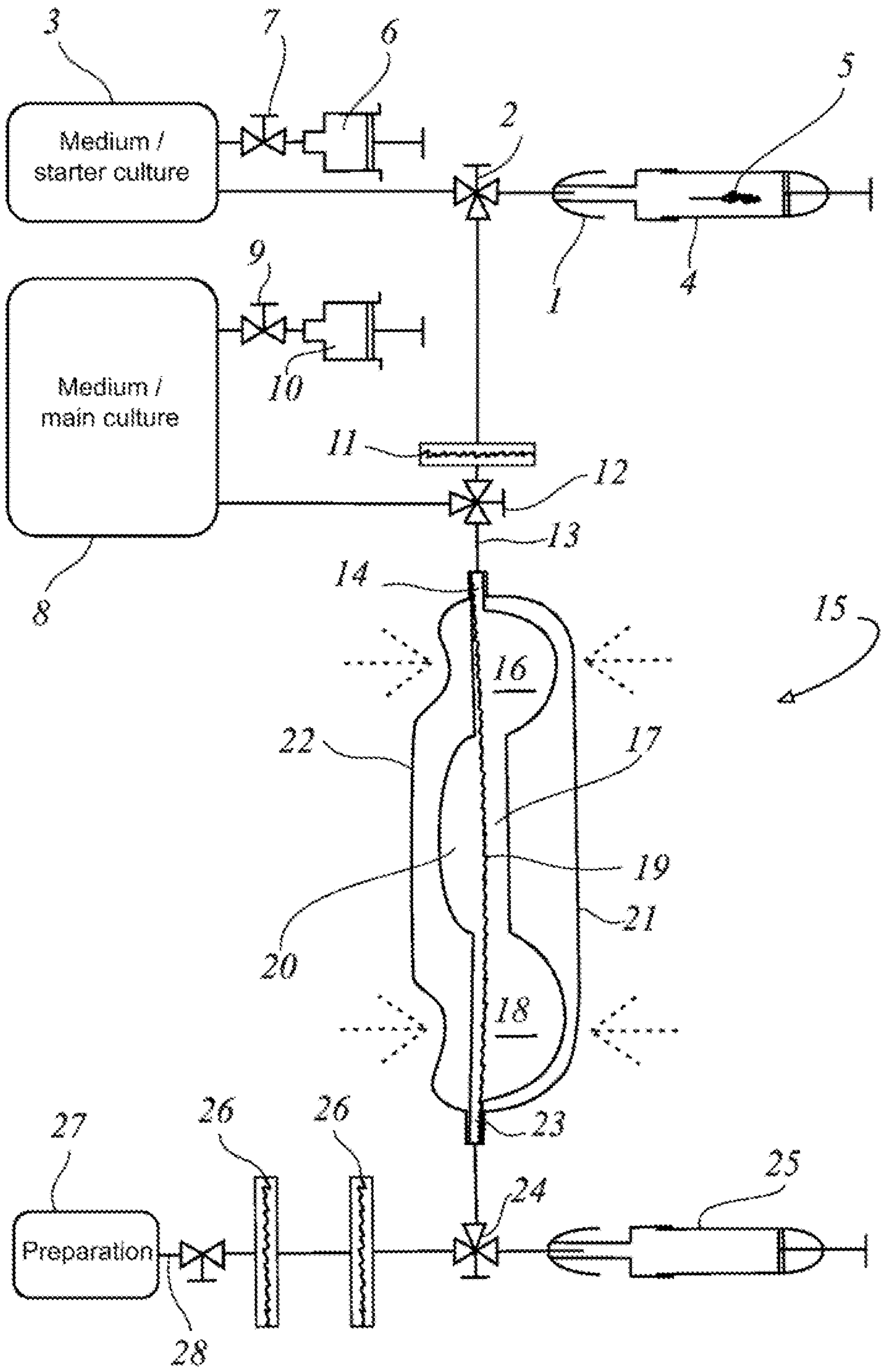
3
7
6
5
Medium / starter culture
2
1
4
9
Medium / main culture
10
11
12
13
8
14
15
16
22
17
19
20
21
18
27
26
26
25
23
24
Preparation
28

PHAGE CULTURING DEVICE, METHOD FOR PREPARING PHAGES, AND FILTRATION DEVICE FOR SAME

The invention relates to a phage culturing device. The invention furthermore relates to a filtration device for use during the preparation of cultured phages, and to a method for culturing phages.

Phages or bacteriophages are viruses that specialize in bacteria as hosts, which adsorb to the bacteria, inject their genome into the bacterial cells, thereby produce copies of themselves within the cell, and, as a result of the copies, cause the hosts to burst, releasing the copies. The phages are highly specific and can therefore also be used well to combat certain bacteria. The so-called phage therapy is thus known in the prior art, which is primarily used in Georgia and the former Soviet Union, for example to combat multiresistant bacteria against which antibiotics otherwise no longer help.

In the Western European countries, the possible use of phages has so far failed, with few exceptions, in light of the hurdles that the necessary protracted approval procedures for phages cultured for therapeutic purposes present for the use as medicinal products. Such hurdles do not exist in the countries of the former Soviet Union. Based on decades of clinical experience, it is thus known from these countries to culture phages specifically for a bacterium, and to then administer these as a therapeutic preparation to the person who is infected with the bacterium. The phages used for multiplication frequently come from the environment, preferably from waste waters, and are therefore presumably also of human origin, but cannot be specifically assigned to one person.

It is an object of the invention to provide a device and a method which open up the option of clinically providing a preparation of autologous phages, which is to say, those that can verifiably be traced back to originating from a very specific person and preferably are also only intended for use in this one specific person. It is an object of the invention to make it possible, by providing a device as a medical product according to the invention, for phages to be autologously produced as an autologous medicinal product according to the German Drug Act and European laws, and to also be used in people within a short time without complicated approval procedures. Regardless of the aforementioned option of preparing autologous phages, however, the invention shall also, in general terms, make it possible to prepare phages on a scale suitable for doctors' practices, while adhering to the highest safety and hygiene requirements.

This object is achieved in that a phage culturing device comprises a fluid line system, which is in particular sealed off, and preferably hermetically sealed, with respect to the outside environment during the entire culturing time, for example by Luer lock connectors.

Potential contact of phages with the environment is preferably possible only when extracting a phage sample, for example from a very specific affected person, and when the phages from the sample are transferred into the culturing device according to the invention. During the entire culturing time and the attendant replication of phages based on the phage sample, any exchange of phages, or also of bacteria, with the environment is precluded according to the invention due to the sealed design of the device.

Such a device according to the invention includes an inlet port to which a sample vessel is connected, or at least can be connected.

In this way, it is ensured that phages from a sample that is inserted/can be inserted into the sample vessel can be transferred via the inlet port into the fluid line system.

When a sample vessel, including the sample of phages present therein, can be connected to the device, the invention can preferably provide that the inlet port is closed until the sample vessel is attached thereto, and in particular is only opened as a result of the sample vessel being attached to the inlet port.

In particular in the case of a sample vessel that is present at the device and into which a sample of phages can be inserted by opening the sample vessel, but also in the case of a connectable sample vessel, the invention can provide that the connection between the interior of the sample vessel including the sample and the interior of the device is not established until negative pressure is established in the sample vessel, for example by increasing the interior volume thereof. This can, for example, only take place when a sample vessel that can be opened so as to insert the sample is closed. The invention can also provide that a sample vessel that can be connected to the device cannot be removed again after the connection has been established, for example by way of a lockable connection. A locking mechanism that cannot be opened again can also be provided in the case of a sample vessel that can be opened/is opened for inserting the sample. These measures can in particular ensure that the device is and remains closed during the entire intended culturing time. This ensures that all phages multiplied as a result of the culturing process can be exclusively attributed to the phages of the sample.

The phages in the sample can preferably stem from a very specific person who is affected by a multiresistant microbe (antibiotic-resistant bacterium). In this case, so-called autologous phages are involved. For example, the phages can be provided by a nasal swab of the particular person. The phages multiplied by way of culturing are thus also all autologous phages in this case. In principle, however, it is also possible to culture phages of arbitrary origin within the scope of the invention.

The device according to the invention furthermore comprises an outlet port, at which a withdrawal vessel is removably attached, or at least can be attached, in particular so that phages, preferably phages multiplied by way of culturing from the phages transferred from the sample, can be withdrawn from the fluid line system via the outlet port.

The invention furthermore comprises a filtration device, which is disposed in a fluid line between the inlet port and the outlet port and which comprises a filter membrane that allows phages to pass in the direction toward the outlet port, while not allowing bacteria to pass. In this way, the phages multiplied in the device can be separated from bacteria, and it can be ensured that a person, or other living beings, to be treated with the multiplied phages cannot be infected with bacteria from the device.

The device of the invention comprises at least one nutrient medium reservoir including a nutrient medium, and at least one host bacteria reservoir including host bacteria, which is in particular closed prior to use and which can be connected to the at least one nutrient medium reservoir by a connecting line that can be opened. The host bacteria can be present in the host bacteria reservoir in lyophilized, viable form or in another form of dormant state.

The nutrient medium is tailored to the host bacteria of the host bacteria reservoir, keeping these alive for the culturing duration.

The nutrient medium is preferably water including a liquid nutrient medium and an energy source that can be utilized for the host bacteria, for example organic compounds or sulfurous compounds, as well as nutrients required by the host bacteria (for example, organic or inorganic carbon, nitrogen, sulfur and phosphate sources as well as other essential nutrients). For example, carbohydrates ("sugar"), protein hydrolysates (peptones), and possibly fatty acids can be provided as nutrients.

As a result of the separation between the nutrient medium reservoir and the host bacteria reservoir, it can furthermore be achieved that a device according to the invention can be stored for almost any arbitrary length of time until use.

This also opens up the option of providing sets of multiple devices according to the invention, in which various devices are implemented, each including different host bacteria, in particular various non-resistant host bacteria of the type of a clinically relevant antibiotic-resistant (hereafter referred to as "resistant") bacterial strain. Following the analysis of a resistant bacterial strain in an affected person, it is possible in this way to select a matching host bacteria strain from devices present in stock.

The reservoirs are preferably only connected once the device is being used.

According to the method, the nutrient medium in the nutrient medium reservoir is mixed with host bacteria, preferably with non-resistant host bacteria from the host bacteria reservoir. These host bacteria are preferably selected as a type strain of a predetermined type of multiresistant bacteria.

For example, it can be provided to analyze the bacterium in a person affected by a multiresistant bacterium, and to select host bacteria that are of a non-resistant kind and of the same bacteria type strain. Such bacteria can, for example, be procured from a bacteria collection. The preferably non-resistant host bacteria are cultured in the nutrient medium, and in particular are reactivated in the process from a lyophilized state or other stage of dormancy.

The connection between the nutrient medium reservoir and the host bacteria reservoir can be achieved by way of a valve, for example. The nutrient medium, for example, which is preferably present in liquid form, can be transferred via the connection into the host bacteria reservoir and be mixed with the host bacteria, whereupon the nutrient medium mixed with bacteria is returned to the nutrient medium reservoir again. This can be carried out, for example, by pressing of the reservoirs, for example manually. This is in particular possible when the reservoirs are implemented as flexible pouches (for example, made of PVC or other plastic materials suitable for blood bags).

According to the invention, the at least one nutrient medium reservoir is disposed upstream from the filtration device in the fluid line system, as viewed in the flow direction from the inlet port to the outlet port.

Phages that are transferred into the fluid line system can thus be replicated at least once, and preferably multiple times, by way of culturing, upstream from the filtration device, in the at least one nutrient medium reservoir including the host bacteria. After the one-time culturing process, or a multiple-culturing process, has been completed, the multiplied phages can then be transported through the filtration device to the outlet port, where they enter the collection vessel.

The invention provides that the nutrient medium mixed with host bacteria is mixed with phages, and in particular with autologous phages from a sample in the sample vessel connected to the fluid line system, which can preferably destroy the multiresistant bacteria that were preferably previously determined by way of analysis, for which purpose the nutrient medium is in particular temporarily transferred into a sample vessel containing the sample and, after contact with the sample, is returned into the nutrient medium reservoir.

During the aforementioned sample collection from the affected person, for example from his or her mucous membrane, it is assumed that the affected person is very likely to already carry phages inside, which have a destroying effect on his or her multiresistant bacteria, however do not find their way via the body of the person to a relevant organ.

So as to transfer phages into the device according to the invention for culturing, it is preferably provided that the inlet port, and in particular the sample vessel connected thereto, can be brought into fluid connection at least temporarily with the at least one nutrient medium reservoir. This can be carried out, for example, by way of a valve, preferably by way of a 3-way valve, which is disposed in the fluid line system between the inlet port and the nutrient medium reservoir.

A three-way valve has the advantage here that a connection between the sample vessel at the inlet port can be switched not only to the described nutrient medium reservoir, but selectively also to other elements of the device, and for example can be conducted to a line containing the nutrient medium mixed with bacteria and phages to the filtration device or further nutrient medium reservoirs. The filter or the filter membrane of the filtration device can preferably have an average pore diameter of less than or equal to 0.45 μm, more preferably less than or equal to 0.2 μm, and still more preferably less than or equal to 0.1 μm.

Preferably, it can be provided that the sample vessel and the at least one nutrient medium reservoir can each be varied in terms of the volumes thereof, in particular that the sample vessel is designed as a syringe, or as a blood collection tube operating according to the aspiration principle or the vacuum principle, and/or the nutrient medium reservoir is designed as a flexible pouch, so that as a result of a change in volume, which can preferably be carried out manually, the nutrient medium, and in particular the nutrient medium that has already been mixed with host bacteria, can be at least temporarily delivered from the at least one nutrient medium reservoir into the sample vessel, and back into the same or a different nutrient medium reservoir.

For sole culturing, or for pre-culturing, the nutrient medium mixed in this way with the phages from the sample can be delivered back into the same nutrient medium reservoir from which the sample came.

For culturing, the entire device can be incubated (for example, in an incubator) for a predetermined time (for example, 10 hours) at a predetermined temperature (for example, 37 degrees Celsius), whereby multiplication of the phages occurs, with lysis of the host bacteria, wherein lysis of the bacteria of the selected type strain replicates exactly those phages that destroy the predetermined multiresistant bacteria. Due to the high specificity of the phages, possibly other phages coming from the sample are advantageously not replicated in this process.

Generally speaking, the phages in the fluid line system obtained after at least one-time culturing are separated from bacteria by way of filtration, and preferably by way of tangential flow filtration (for example, in a downstream single-use filtration chamber, which will be described in greater detail hereafter, which was in particular produced using a blistering method). The phages separated by way of filtration are transferred into a collection vessel that is connected to the fluid line system and are preferably removed from the fluid line system, using the collection vessel, as a usable, preferably autologous preparation.

The invention at least provides culturing the phages stemming from the sample at least once, selectioning and replicating these in the process. The number of phages obtained thereby may possibly not be sufficient.

The invention can thus also provide, in a preferred embodiment, that the culturing of the phages is repeated at least once, in particular using a new batch of nutrient medium and a new batch of the same host bacteria present in the device according to the invention in further reservoirs.

In a preferred embodiment, multiple nutrient medium reservoirs can be disposed upstream from the filtration devices, as viewed in the flow direction from the inlet port to the outlet port, which, in the flow direction, are consecutively connected to a connecting line leading to the filtration device, in particular in each case via a switchable 3-way valve, and preferably in such a way that a change in volume of the sample vessel or of a nutrient medium reservoir allows the nutrient medium to be withdrawn from one of the nutrient medium reservoirs and transferred into a nutrient medium reservoir situated downstream in the flow direction. In this way, the nutrient medium of a downstream reservoir, which has preferably already been provided with host bacteria, can be inoculated with the cultures of phages of a preceding reservoir.

Preferably, a respective dedicated host bacteria supply is assigned to each of several nutrient medium reservoirs, which in particular can only be brought in connection with the nutrient medium of the assigned nutrient medium reservoir directly at the assigned nutrient medium reservoir by a closed connecting line that can be opened. The host bacteria of all host bacteria reservoirs of a device thus refined are all of the same type strain, and the host bacteria of all host bacteria reservoirs are in particular the same.

More preferably, a sterile filter is disposed between two nutrient medium reservoirs situated consecutively in the flow direction.

A sterile filter shall be understood to mean a filter that is suitable for retaining bacteria and bacterial fragments. In the application described here, in contrast, phages are able to pass the sterile filter. The filter membrane of a sterile filter can preferably have an average pore diameter of less than or equal to 0.45 μm, more preferably less than or equal to 0.2 μm, and still more preferably less than or equal to 0.1 μm.

In this way, phages can be transferred together with the nutrient medium from one of multiple nutrient medium reservoirs, preferably via a sterile filter, into the nutrient medium of a further nutrient medium reservoir, which was previously mixed with host bacteria of the same selected type strain, for repeating the culturing at least once, prior to the filtration. In this way, a further culturing process, and accordingly further replication, are carried out. According to the invention, culturing twice is preferred, however it may also be provided that the culturing step described is carried out an even greater number of times.

Ultimately, separation of the multiplied, preferably autologous phages from the bacteria in the nutrient medium is carried out at the end of the culturing step by the filtration devices mentioned at the outset.

The filtration device is particularly preferably designed as a tangential flow filtration device, in which the nutrient medium flows tangentially across the filter membrane, in particular in a reversing manner, on one of the two membrane sides.

In this way, solid accumulation of bacteria at the membrane is prevented, or at least delayed, and the filtration efficiency is increased.

The filtration device, which is preferably designed as a tangential flow filtration device, can preferably comprise a first cavity and a second cavity having a variable, preferably manually variable, volume, which are connected to one another by way of at least one channel, and preferably multiple parallel channels, the wall of which is formed by a filter membrane at least in regions, across which nutrient medium, which can be pumped back and forth between the first and second cavities, can flow tangentially at the first side thereof pointing toward the channel interior, and which at the second side thereof facing away from the channel interior adjoins a third cavity, wherein an inlet channel opens into the first cavity, and an outlet channel opens into the third cavity.

The inlet channel opening into the first cavity can form the end of the fluid line of the system according to the invention, through which the phages, together with the nutrient medium, are fed to the filtration device after culturing. In one embodiment, for example, this feeding can take place purely by way of gravity, or it can take place by reducing the volume of the nutrient medium reservoir in which the most recent culturing step, or possibly also the only culturing step, has taken place. The outlet channel of the filtration device leads in the direction of the collection vessel of the device, for example directly, or also indirectly, via a fluid-delivering element.

Regardless of the specific design of the filtration device, the membrane is preferably configured in such a way that only phages are able to pass through the membrane, while bacteria and the residues thereof, created by lysis, are held back by the membrane. The filter membrane of the filtration device can preferably have an average pore diameter of less than or equal to 0.45 μm, more preferably less than or equal to 0.2 μm, and still more preferably less than or equal to 0.1 μm.

For example, the invention can provide that the first and second cavities are alternately reduced in terms of the respective volume thereof, for example by manual pressing onto the flexible cavity (for example, made of polypropylene or another plastic material), whereby a reversing fluid flow of the nutrient medium including the multiplied phages is achieved, and the phages, after filtration, accumulate in the third cavity, which is preferably disposed on the other membrane side, based on the flow direction between the first and second cavities.

It may be provided here that the first cavity, the second cavity, the inlet channel, and the at least one channel connecting the cavities are integrally formed into a first foil, and in particular are integrally formed as a bulge protruding from the foil plane, and the third cavity and the outlet channel are integrally formed into a second foil, and in particular are integrally formed as a bulge protruding from the foil plane, wherein the first and second foils are attached, in particular welded or laminated, from opposing sides to the surfaces of a filter membrane. This foil can be made of the described polypropylene or another plastic material.

This results in a filtration device that has a manual pump function and can easily be manually actuated as a result of the flexibility of the foils. The invention can also provide that the volumes of the cavities are also compressed by way of actuators.

For safety reasons, the invention can also provide that each of the two foils is covered by a flexible shell, which is tightly attached, in particular by lamination/welding, to the respective foil, in particular along the edge of the filter membrane.

An embodiment of the invention will be described in more detail based on the drawing.

The invention preferably utilizes a two-stage phage enrichment method including downstream sterile filtration and filling, utilizing the illustrated device. The device according to the invention shown in the drawing comprises a system including fluid lines, pouches, and filters.

The device includes an inlet port 1, which is connected to a nutrient medium reservoir 3 by way of a three-way valve 2 and to which, for example, a so-called Monovette, serving as the sample vessel 4, can be connected, which receives a swab tip of a nasal swab from a patient affected by multiresistant bacteria. The swab tip represents a sample 5 containing phages, which the patient who is to be treated later personally carries inside (for example, as a non-autologous immune system).

The three-way valve 2 is connected via a line to the nutrient medium reservoir 3, which can, for example, be embodied by a blood bag, here for the preculture of the phages from the swab tip 5. This nutrient medium pouch 3 is, in turn, connected to a host bacteria reservoir 6 including a host bacteria supply, for example in a disposable syringe, via a valve 7, in which lyophilized but viable host bacteria are kept available. These host bacteria were selected as the type strain of the multiresistant microbe from which the patient suffers from whom the nasal swab on the swab sample was taken.

The host bacteria were, for example, previously procured from a recognized collection and do not have any resistance to antibiotics whatsoever. When the sample vessel 4 is being connected to the three-way valve 2, first the valve 7 between the host bacteria reservoir 6 and the nutrient medium pouch 3 is opened, and the lyophilized host bacteria are reactivated and flushed back into the pouch 3 by the nutrient medium being suctioned in from the pouch 3. After a preferably implemented preculturing duration of several hours at a suitable incubation temperature (for example, 37° C.), the three-way valve 2 is opened, and the activated microbes/host bacteria are drawn into the sample vessel 4 by an increase in the volume of the sample vessel 4.

There, phages from the nasal swab may adsorb to the reactivated host bacteria when the flow around the swab tip 5 occurs. Subsequent incubation, for example, overnight, gives the phages present in the sample the opportunity to lyse the bacteria culture that is subsequently infected. Only the phages that are compatible with these host bacteria are replicated.

The nutrient medium is, likewise preferably overnight, suctioned from a further nutrient medium reservoir 8, which is connected to the device of the invention, which is preferably designed as a disposable device, via a valve 9 that is opened for this purpose into a second host bacteria reservoir 10, which is only connected to this pouch 8 and, for example, embodied by a syringe. The lyophilized host bacteria of the same type strain as described above that are kept available in this host bacteria reservoir 10 are reactivated by the nutrient medium and are subsequently injected back into the nutrient medium reservoir 8 designed as a main culture pouch. There, the bacteria can replicate, for example overnight, while the same bacteria in the starter culture are lysed, provided that lytic phages were present in the nasal swab.

Thereafter, the infected host bacteria culture is drawn up from the nutrient medium reservoir 3 of the starter culture into the sample vessel, for example the Monovette, through the three-way valve 2, and, after the valve has been switched or the starter culture pouch 3 has been pinched off, is filtered through a sterile filter 11, which is likewise preferably connected to the three-way valve 2, by being pressed out of the sample vessel 4. The phages, which have preferably been produced overnight in the starter culture, pass the sterile filter 11 and, through an appropriately opened second three-way valve 12 downstream from the sterile filter 11, reach the main culture in the pouch of the further nutrient medium reservoir 8 which, for example, has replicated overnight.

The phages that have preferably replicated overnight from the starter culture can now, in the main culture pouch 8, infect the host bacteria of the type strain that is not antibiotic-resistant, which have likewise replicated there, and can be replicated to a much greater extent during the incubation, for example over the course of a second night, by virtue of lysis of the host bacteria.

After the second three-way valve 12 has been switched, the corresponding lysate, including phages, is then conducted into the tangential flow filter 15, for example by way of gravitation, via a feed line 13 and the inlet channel 14 of the tangential flow filter. There, the lysate fills at least the first cavity 16, which is connected to the second cavity 18 by at least one channel, and preferably multiple channels 17. At least the channel is connected via a filter medium 19, which is to say through the pores of the filter membrane, to a third cavity 20. In the filter 15, a strong tangential flow is generated in the at least one channel 17 above the filtration membrane 19 by alternately pressing in the two flexible, retentate-side cavities 16 and 17. Two enveloping plastic shells 21 and 22 that are sealed on ensure that no host bacteria can exit the device, even in the event that one of the cavities 16, 18 or 20 bursts.

Due to the filtration principle of tangential flow filtration, efficient separation of the replicated phages from the cell debris, which advantageous arose overnight due to lysis, and the still intact host bacteria is achieved. The permeate is collected in the permeate-side cavity 20 of the tangential flow filter 15 and is subsequently drawn into a preferably provided syringe 25 via the outlet channel 23 through a third three-way valve 24.

After the third three-way valve 24 has been switched, the permeate is preferably pressed through two sterile filters 26, which are connected in series, downstream from the three-way valve 24 by way of syringe pressure. This phage-containing sterile filtrate is collected in a connected collection vessel, for example a preparation pouch 27, and is separated by the device according to the invention, preferably a disposable device, after the valve 24 has been closed. The preparation pouch 27 is attached to an outlet port of the device so as to be removable for this purpose.

The inlet port 1 and the outlet port 28 can be formed, for example, by Luer lock connectors.

The preferably autologous phage preparation that is produced in this first application example can be used as a patient-specific formulation for novel medical therapies, such as the phage therapy.

In a second application example, phage preparations are produced according to the same principle from environmental samples containing type strains of multiresistant microbes from large-scale livestock farming and are admixed to the animal feed as an animal feedstuff supplement to prevent the spread of multiresistant microbes.

In a third preferred application example, phage preparations produced according to the same principle are sprayed on infected plantations to combat bacterial plant diseases.

In a fourth preferred application example, phage preparations produced according to the same principle are sprayed onto commercially available foodstuffs or in foodstuff production facilities to combat spoiling agents and pathogens.

The invention claimed is:

1. A phage culturing device, comprising a fluid line system that is sealed off with respect to the outside environment, comprising:

a. an inlet port configured to have a sample vessel connected thereto in such a way that phages from a sample that is inserted into the sample vessel can be transferred via the inlet port into the fluid line system;

b. an outlet port configured to have a withdrawal vessel removably attached thereto so that the phages can be withdrawn from the fluid line system via the outlet port;

c. a filtration device disposed in a fluid line between the inlet port and the outlet port and comprises a filter membrane configured to allow the phages to pass in a direction toward the outlet port, while not allowing bacteria to pass;

d. at least one nutrient medium reservoir including a nutrient medium; and e. at least one host bacteria reservoir including host bacteria in lyophilized, viable form and which is closed prior to use and which is configured to be connected to the at least one nutrient medium reservoir by a connecting line that is configured to be opened, the at least one nutrient medium reservoir being disposed upstream from the filtration device in the fluid line system, as viewed in a flow direction form the inlet port to the outlet port so that the phages that are transferred into the fluid line system can be replicated at least once by way of culturing upstream from the filtration device in the at least one nutrient reservoir including the host bacteria, wherein the filtration device is a tangential flow filtration device configured to cause the nutrient medium to flow tangentially across the filter membrane in a reversing manner on one of two sides of the membrane, and wherein the tangential flow filtration device comprises a first and a second cavity each having a variable volume and being connected to one another by way of at least one channel at regions of a wall which are formed by the filter membrane and the at least one channel is configured so that across the at least one channel nutrient medium can be pumped back and forth between the first and second cavities and can flow tangentially at a first side of the wall pointing toward the channel interior and which at a second side of the wall facing away from an interior of the at least one channel adjoins a third cavity, an inlet channel opening into the first cavity and an outlet channel opening into the third cavity.

2. The device according to claim 1, wherein the first cavity, the second cavity, the inlet channel and the at least one channel connecting the first and second cavities are integrally formed into a first foil as a bulge protruding from a plane of the first foil and the third cavity and the outlet channel are integrally formed into a second foil as a bulge protruding from a plane of the second foil, the first and second foils being welded or laminated, from opposing sides to surfaces of the filter membrane.

3. The device according to claim 2, wherein each of the two foils is covered by a respective flexible shell which is attached to the respective foil by lamination or welding.

* * * * *